United States Patent [19]

Ruckes et al.

[11] Patent Number: 4,902,825
[45] Date of Patent: Feb. 20, 1990

[54] N,N'-BIS(TRANS-4-ISOCYANATOCY-CLOHEXYL)UREA, A PROCESS FOR ITS PREPARATION AND ITS USE

[75] Inventors: Andreas Ruckes, Leverkusen; Werner Rasshofer; Richard Kopp, both of Cologne; Gerhard Grögler, Leverkusen, all of Fed. Rep. of Germany

[73] Assignee: Bayer Aktiengesellschaft, Bayerwerk, Fed. Rep. of Germany

[21] Appl. No.: 255,915

[22] Filed: Oct. 11, 1988

[30] Foreign Application Priority Data

Oct. 20, 1987 [DE] Fed. Rep. of Germany ....... 3735469

[51] Int. Cl.$^4$ .................... C07C 69/00; C07C 127/15
[52] U.S. Cl. ..................................... 560/330; 564/57; 528/159
[58] Field of Search .......................... 560/330; 564/57

[56] References Cited

U.S. PATENT DOCUMENTS 3,023,228  2/1962  Wegner et al. .................... 560/330

OTHER PUBLICATIONS

S. W. Wong and K. C. Frisch, Advances In Urethane Science And Technology, vol. 8, pp. 75–92, 1981.

Primary Examiner—Alan Siegel
Attorney, Agent, or Firm—Joseph C. Gil; Richard E. L. Henderson

[57] ABSTRACT

The present invention relates to N,N'-bis-(4-isocyanatocyclohexyl)urea obtained from the reaction with water of cyclohexane-1,4-diisocyanate having a high trans isomer content. This invention further relates to the process for preparing the N,N'-bis(4-isocyanatocyclohexyl)urea and to its use in the synthesis of polyurethanes.

5 Claims, No Drawings

N,N'-BIS(TRANS-4-ISOCYANATOCYCLOHEXYL-)UREA, A PROCESS FOR ITS PREPARATION AND ITS USE

BACKGROUND OF THE INVENTION

The present invention relates to N,N'-bis-(trans-4-isocyanatocyclohexyl)urea obtained by the reaction in an inert solvent of a cyclohexane-1,4-diisocyanate ("CHDI") having a high transisomer content and water. The urea according to the invention, which may contain a small portion of oligomeric ureas, may advantageously be used for the synthesis of polyurethanes.

It is known that monoisocyanates react with water to form N-substituted carbamic acid derivatives which can be converted into urea derivatives, with concomitant liberation of carbon dioxide, by a reaction with further quantities of isocyanate. Polyureas are obtained analogously from diisocyanates and water by polyaddition.

It is also known that under certain reaction conditions, low molecular weight urea diisocyanates of the following general formula

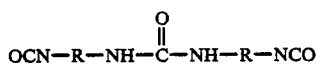

may be isolated from the reaction mixture obtained when 1 mol of water reacts with at least 2 mol of a diisocyanate at low temperatures (that is, about 0° to 30° C.) in a solvent. According to DAS No. 1,101,394, only those diisocyanates in which the two isocyanate groups differ in their reactivity, for example, 2,4-tolylenediisocyanate, are suitable for this reaction. Aliphatic diisocyanates are less suitable because of their low reactivity with water. Thus, although urea diisocyanates have already been described generally, no diisocyanato urea based on CHDI has been described specifically.

When attempts are made to react commercial CHDI with water in an inert solvent under the usual conditions previously known in the art, only small quantities of polymeric urea with low NCO content are obtained, even when basic catalysts and long reaction times are employed. This observation is also in agreement with the formation of urea described by S. W. Wong and K. C. Frisch in *Adv. in Urethane Sci. and Technol*, 8, 75-92 (1981), their account of a kinetic investigation. According to Wong and Frisch, the reaction of highly dilute solutions of trans-CHDI with water in cellosolve acetate at 50° C. resulted in a polyurea with a half life of 3623 minutes and an isocyanate content approaching 0%.

It has now surprisingly been found that N,N'-bis(4-isocyanatocyclohexyl)urea (optionally containing only a small proportion of oligomeric ureas) may be obtained in a high yield when cyclohexane-1,4-diisocyanate having a high transisomer content reacts with water in a molar ratio of 2:1 at low temperatures (about 40° C.) in inert solvents at a concentration of 10% by weight (based on the solvent used) in the presence of basic catalysts.

The urea according to the invention can advantageously by used for the synthesis of polyurethane elastomers which have excellent mechanical properties as well as outstanding thermal stability. Moreover, the unpleasant properties of the starting diisocyanates, namely the pungent odor and lachrymatory effect due to the low vapor pressure, do not occur in the corresponding urea, so that it can advantageously be processed more simply and safely.

SUMMARY OF THE INVENTION

The present invention relates to N,N'-bis(4-isocyanatocyclohexyl)urea, of the Formula I,

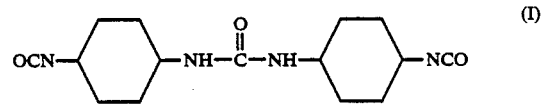

optionally containing a small proportion of oligomeric ureas, obtainable from the reaction of cyclohexane-1,4-diisocyanate having a high transisomer content with water under the conditions detailed below. The present invention further relates to a process for the preparation of the compound of Formula I and to its use in the synthesis of polyurethanes.

DESCRIPTION OF THE INVENTION

The cyclohexane-1,4-diisocyanate used for the preparation of the urea according to the invention has a high transisomer content, the proportion of which is at least about 80% by weight (preferably at least 90% by weight) based on the CHDI. The proportion is more preferably at least 95% by weight and most preferably at least 99% by weight. The CHDI should preferably consist substantially of the transisomers; that is, the proportion of cis isomers is zero or at least negligibly small. The starting component used for the process according to the invention may be, for example, trans-cyclohexane-1,4-diisocyanate prepared by the process described in DE-PS No. 2,710,595.

The solvents used are those in which the CHDI and at least a portion of the water required are soluble. Such solvents should also be free from isocyanate reactive groups so as to be substantially inert or unreactive towards isocyanates. Suitable solvents include ethers such as diethyl or diisopropyl ether, ketones such as acetone or methylethly ketone, and esters such as isopropyl acetate or cellosolve acetate. Although solvents in which water is virtually insoluble (halogenated hydrocarbons, for example) are unsuitable as solvents for this invention, it is not necessary for the total quantity of water required to dissolve in the solvent used. Diisopropyl ether, methylethyl ketone, and cellosolve acetate are preferred solvents.

The concentration of CHDI in the solvent is generally not critical but if the dilution is excessive the urea obtained may have a greatly reduced isocyanate content. The concentration of CHDI is preferably ≧10% by weight, especially ≧30% by weight, based on the solvent, but if the solutions are too highly concentrated there is a risk that the reaction product will be contaminated with unreacted CHDI.

The quantity of water is substantially equal to the theoretically required quantity for reacting with two isocyanate groups. If too little water is used, unreacted starting isocyanate is left in the reaction mixture and must be removed. If too much water is used, the polyurea obtained has a greatly reduced isocyanate content.

The urea obtained is virtually insoluble in the solvents mentioned above and therefore will essentially not take part in any further reaction between isocyanate groups still present and water. Thus, in general, only one isocyanate group per molecule of the CHDI put into the process takes part in the formation of urea groups.

The reaction temperature should generally be kept below 55° C. At higher reaction temperatures, the solubility of the urea increases so that it is likely to undergo further reaction with water to form polymers or oligomers of ureas.

If satisfactory yields in reasonable times are to be obtained, it is necessary to use a catalyst to accelerate the reaction between water and the rather slowly reacting aliphatic CHDI. The catalysts used are preferably those conventionally used in polyurethane chemistry, for example, tertiary amines (such as N,N-dimethylbenzylamine, triethylamine, diazabycyclooctane) or organometallic compounds (such as tributyltin acetate, dibutyltin diacetate, tin(II) dioctoanoate, dibutyltin dilaurate. The quantity of catalyst is preferably selected so that the heat evolved in the reaction will not warm the mixture to a temperature above about 40° C., thereby eliminating the need for external cooling.

After completion of the reaction, the precipitated product is suction filtered through a suitable filter, washed with an inert solvent (e.g. acetone or petroleum ether), and dried at a low temperature in a drying oven, preferably under vacuum.

The isocyanate content of the product obtained by this process is normally only slightly below the calculated isocyanate content. However, if satisfactory yields are to be obtained in reasonable times, the reaction conditions must generally be selected so that the isocyanate content of the products obtained is less than the theoretical content, thereby allowing slight oligourea formation to take place. All measures which increase the reaction velocity, such as elevated temperature, increased quantities of catalyst, and the use of polar water soluble solvents, will increase the yields at shorter reaction times but at the same time will invariably reduce the isocyanate content of the urea of the invention. Such products may be used, however, provided the formation of oligourea by-product does not exceed certain limits.

The urea end product, which is stable in storage and easy to handle, is obtained in the form of a finely divided crystalline powder in yields of up to 85% and with isocyanate contents of at least 21%, depending on the reaction conditions.

The urea according to the invention may advantageously be used in its low molecular weight and low oligomeric form for the synthesis of polyurethane systems. A preferred application involves the preparation of casting elastomers in which polyethers and, most preferably, polyesters terminated with aromatic amino groups are used as the isocyanate reactive components. These are preferably obtained according to EP-AS No. 219,035 by the hydrolysis of compounds containing terminal isocyanate groups. In this process, polyethers and polyesters, especially of the type containing two or three hydroxyl groups, are first converted into isocyanate prepolymers. In a second step, the isocyanate groups are converted into amino groups by hydrolysis. Elastomers with outstanding heat resistance and excellent mechanical properties are obtained.

The following examples further illustrate the preparation of ureas according to the invention and their use in the preparation of high quality polyurethane elastomers. The invention, which is set forth in the foregoing disclosure, is not to be construed or limited either in spirit or in scope by these examples. Those skilled in the art will readily understand that known variations of the conditions and processes of the following preparative procedures can be used. Unless otherwise indicated, all percentages are percentages by weight and all temperatures are degrees Celsius unless otherwise noted. The cyclohexane-1,4-diisocyanate ("CHDI") used in the examples according to the invention was trans-cyclohexane-1,4-diisocyanate manufactured by Akzo, Wuppertal, West-Germany ("Elate 166" ®), unless otherwise indicated.

DESCRIPTION OF THE PREFERRED EMBODIMENTS

EXAMPLE 1

CHDI (830 g, 5 mol) is dissolved in 2,000 g of methylethyl ketone ("MEK"). After the addition of a solution of 46 g (2.56 mol) of water in 250 ml of 1:1 MEK-acetone and 0.9 g of N,N-dimethylbenzylamine, the reaction mixture is stirred at room temperature for 60 hours. The precipitated product is suction filtered and washed, first with acetone and then with petroleum ether, and freed from solvents in a vacuum drying oven. The product is obtained as a finely divided crystalline powder in a yield of 666 g (87% based on the CHDI used in the process) with an isocyanate content of 22.9% by weight.

Elemental analysis. Calc: C, 58.8; H, 7.2; N, 18.3 Found: C, 58.4; H, 7.7; N, 18.5

EXAMPLE 2

CHDI (166 g, 1 mol) is dissolved in 480 g of diisopropyl ether. After the addition of a solution of 9.8 g (0.51 mol) of water in 80 g of acetone and 0.21 g of N,N-dimethyl-benzylamine, the reaction mixture is stirred at room temperature for 7 days. The precipitated product is suction filtered, washed with acetone, and freed from solvent in a vacuum drying oven. The product is obtained in a yield of 43 g (28%) with an isocyanate content of 26.6% by weight.

Elemental analysis. Calc.: C, 58.8; H, 7.2; N, 18.3 Found: C, 58.4, H, 7.6; N, 18.4

EXAMPLE 3

CHDI (83 g, 0.5 mol) is dissolved in 250 ml of ethylene glycol ethyl ether acetate ("EGA"). After the addition of a solution of 4.6 g (0.256 mol) of water in 25 ml of 1:1 EGA/acetone and 0.09 g of N,N-dimethylbenzylamines, the reaction mixture is stirred at room temperature for 19 hours. The precipitated product is suction filtered, washed with acetone, and freed from solvent in a vacuum drying oven, yielding 10 g (13%) of the product having an isocyanate content of 27.1% by weight.

EXAMPLE 4

CHDI (83 g, 0.5 mol) is dissolved in 250 ml of EGA. After the addition of a solution of 4.6 g (0.256 mol) of water in 25 ml of 1:1 EGA/acetone and 1.87 g of diazabicyclo[2.2.2]octane ("DABCO"), the reaction mixture is stirred at room temperature for 19 hours. The mixture is worked up as in Example 2 to give 65 g (85%) of the product with an isocyanate content of 22.0% by weight.

EXAMPLE 5

Comparison example (not according to the invention) using non-stoichiometric quantity of water in high dilution.

CHDI (9.71 g, 0.058 mol) is dissolved in 250 ml of EGA. After the addition of a solution of 1.08 g (0.06 mol) of water in 250 ml of EGA and 0.22 g of DABCO, the reaction mixture is stirred at 50° C. for 19 hours. No precipitation of product was observed during this time.

EXAMPLE 6

Comparison example (not according to the invention) performed as in Example 5 but at a higher concentration.

CHDI (40.4 g, 0.24 mol) is dissolved in 125 ml of EGA. After the addition of a solution of 4.5 g (0.25 mol) of water in 125 ml of EGA and 0.93 g of DABCO, the reaction mixture is stirred at 50° C. for 19 hours. The mixture is worked up as in Example 3 to give 15 g (40.8%) of a polymeric urea which no longer contains any detectable isocyanate groups.

EXAMPLE 7

Same as Example 5 but with the stoichiometrically correct quantity of water.

CHDI (19.4 g, 0.116 mol) is dissolved in 500 ml of EGA. After the addition of a solution of 1.08 g (0.06 mol) of water in 500 ml of EGA and 0.44 g of DABCO, the reaction is stirred at 50° C. for 60 hours. The mixture is worked up as in Example 3 to give 4.7 g (26.5%) of a urea having an isocyanate content of 14.5% by weight.

EXAMPLE 8

Comparison example (not according to the invention).

A cyclohexane-1,4-diisocyanate composition (166 g, 1 mol) composed of 37.2% by weight of the cis-isomer and 62.8% by weight of the trans-isomer are dissolved in 400 g of MEK. After the addition of a solution of 9.2 g (0.51 mol) of water in 50 ml of 1:1 MEK/acetone and 0.18 g of N,N-dimethylbenzylamines, the reaction mixture is stirred at room temperature for 60 hours. The mixture is worked up as in Example 1 to give 110 g (71.9%) of an oligomeric urea having an isocyanate content of 8.7% by weight.

EXAMPLE 9

Comparison example (not according to the invention).

A cyclohexane-1,4-diisocyanate composition (166 g, 1 mol) composed of 83% by weight of the cis-isomer and 16% by weight of the trans-isomer are dissolved in 800 g of MEK. After the addition of a solution of 9.2 g (0.51 mol) of water in 50 ml of acetone and 0.18 g of N,N-dimethylbenzylamine, the reaction mixture is stirred at room temperature for 19 hours. Since no precipitation of product can be observed, stirring is continued for a further 24 hours at 50° C. It is only after a total of 4.5 g of N,N-dimethylbenzylamine have been added and the reaction is continued for a further 60 hours that working up the reaction product in the usual manner yields 73 g (47.7%) of a urea having an isocyanate content of 16.0% by weight.

EXAMPLE 10

Preparation of a polyurethane elastomer by the casting elastomer technique.

The polyester with aromatically bound amino end groups used in this example was prepared according to EP-AS No. 219,035 by hydrolysis of an isocyanate prepolymer having an isocyanate content of 3.66% and which in turn had been prepared from a polyester based on adipic acid, ethylene glycol with OH number 56, and 2,4-diisocyanato toluene, using an equivalent ratio of NCO:OH of 2:1.

The above described amino polyester (200 g) is mixed at 50°–60° C. with CHDI urea product (34.7 g) from Example 1 in the form of a ground powder (particle size 10–30 μm), and then thoroughly homogenized and degassed in a water jet vacuum. A reactive system is obtained which has a pot life at 50°–60° C. of several hours without any untoward increase in viscosity during this period.

This readily pourable reactive system is and treated with mold release agent. The mold is then heated to 110°–150° C. After the reaction mixture has solidified (1 to 2 hours), the molded part obtained is removed and tempered for about 2 hours at 120° C. The high quality polyurethane elastomer thus obtained has excellent thermal stability and the mechanical properties shown below.

| Tensile strength | (DIN 53504) | 28.7 MPa |
| Elongation at break | (DIN 53504) | 500% |
| Tear propagation resistance | (DIN 53515) | 80.5 KN/m |
| Shore A hardness | (DIN 53505) | 97 |
| Elasticity | (DIN 53512) | 40% |

What is claimed is:

1. A compound of the formula

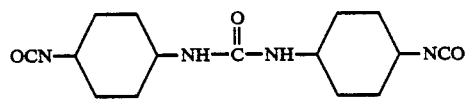

wherein the trans isomer N,N'-bis(trans-4-isocyanatocyclohexyl)urea comprises at least 80% by weight of said compound.

2. A compound according to claim 1 wherein the trans isomer N,N'-bis(trans-4-isocyanatocyclohexyl)urea comprises at least 90% by weight of said compound.

3. A compound according to claim 1 which is N,N'-bis(trans-4-isocyanatocyclohexyl)urea.

4. A compound according to claim 1 wherein the trans isomer N,N'-bis(trans-4-isocyanatocyclohexyl)urea has an isocyanate content of at least 1% by weight.

5. A composition comprising a compound according to claim 1 in combination with an oligourea by-product.

* * * * *